(12) United States Patent
Gaffney et al.

(10) Patent No.: US 10,227,538 B2
(45) Date of Patent: Mar. 12, 2019

(54) FACILITATED OXYGENATE SEPARATIONS AND SYNTHETIC FUEL PRODUCTION VIA REACTIVE DISTILLATION

(71) Applicant: GAS TECHNOLOGIES LLC, Walloon Lake, MI (US)

(72) Inventors: Ian Lawrence Gaffney, Los Gatos, CA (US); Walter Breidenstein, Boyne Falls, MI (US); Evan Michael Visser, Hull, IA (US)

(73) Assignee: GAS TECHNOLOGIES LLC, Walloon Lake, MI (US)

( * ) Notice: Subject to any disclaimer, the term of this patent is extended or adjusted under 35 U.S.C. 154(b) by 0 days.

(21) Appl. No.: 15/126,432

(22) PCT Filed: Mar. 16, 2015

(86) PCT No.: PCT/US2015/020740
§ 371 (c)(1),
(2) Date: Sep. 15, 2016

(87) PCT Pub. No.: WO2015/142727
PCT Pub. Date: Sep. 24, 2015

(65) Prior Publication Data
US 2017/0081602 A1 Mar. 23, 2017

Related U.S. Application Data

(60) Provisional application No. 61/953,826, filed on Mar. 15, 2014.

(51) Int. Cl.
*C10L 1/02* (2006.01)
*C07C 51/00* (2006.01)
(Continued)

(52) U.S. Cl.
CPC .............. *C10L 1/026* (2013.01); *C07C 29/00* (2013.01); *C07C 41/50* (2013.01); *C07C 45/28* (2013.01);
(Continued)

(58) Field of Classification Search
CPC combination set(s) only.
See application file for complete search history.

(56) References Cited

U.S. PATENT DOCUMENTS

| 2,710,829 A | 5/1947 | Michael |
| 4,399,305 A | 8/1983 | Schreck |

(Continued)

OTHER PUBLICATIONS

Gornay, J. et al., "Direct Conversion of Methanol into 1,1-Dimethoxymethane: Remarkably High Productivity Over an FeMo Catalyst Placed Under Unusual Conditions," Green Chem., 2010, 12, pp. 1722-1725.

(Continued)

*Primary Examiner* — Ellen M McAvoy
*Assistant Examiner* — Chantel L Graham
(74) *Attorney, Agent, or Firm* — Brooks Kushman P.C.

(57) ABSTRACT

A method includes a step of reacting a hydrocarbon-containing gas with an oxygen-containing gas to form a first product blend in a reactor. The first product blend includes a blend of partially oxygenated compounds. The blend of partially oxygenated compounds is provided to one or more reactive distillation stations; and The blend of partially oxygenated compounds is converted to a second product blend at one or more reactive distillation stations. Characteristically, the second product blend includes a mixture comprising a at least two of components selected from acetals, ethers, alcohols, esters, and alkenes.

28 Claims, 2 Drawing Sheets

(51) Int. Cl.
  *C07C 29/00* (2006.01)
  *C07C 67/00* (2006.01)
  *C07C 45/28* (2006.01)
  *C07C 41/50* (2006.01)

(52) U.S. Cl.
  CPC .............. *C07C 51/00* (2013.01); *C07C 67/00* (2013.01); *C10L 2290/543* (2013.01)

(56) References Cited

U.S. PATENT DOCUMENTS

| | | | |
|---|---|---|---|
| 4,501,917 | A | 2/1985 | Schmidt et al. |
| 4,579,980 | A | 4/1986 | Kogoma et al. |
| 4,620,050 | A | 10/1986 | Cognion et al. |
| 5,579,980 | A | 12/1996 | Ichikawa |
| 5,773,669 | A | 6/1998 | Shimasaki et al. |
| 6,090,988 | A * | 7/2000 | Kambe ............... C07C 41/42 502/240 |
| 7,456,327 | B2 | 11/2008 | Pawlak et al. |
| 7,578,981 | B2 | 8/2009 | Pawlak et al. |
| 7,642,293 | B2 | 1/2010 | Pawlak et al. |
| 7,687,669 | B2 | 3/2010 | Pawlak et al. |
| 7,772,423 | B2 | 8/2010 | Celik et al. |
| 7,879,296 | B2 | 2/2011 | Pawlak et al. |
| 7,910,787 | B2 | 3/2011 | Pawlak et al. |
| 8,193,254 | B2 | 6/2012 | Pawlak et al. |
| 8,202,916 | B2 * | 6/2012 | Pawlak ............... B01J 19/2415 422/187 |
| 8,293,186 | B2 | 10/2012 | Pawlak et al. |
| 2002/0026744 | A1 | 3/2002 | Golubkov et al. |
| 2007/0130822 | A1 | 6/2007 | Araya |
| 2009/0069607 | A1 * | 3/2009 | Smith, Jr. ............... C07C 41/09 568/671 |
| 2012/0232311 | A1 | 9/2012 | Hsieh et al. |
| 2013/0109891 | A1 | 5/2013 | Lee et al. |

OTHER PUBLICATIONS

Gornay, J. et al., "Direct Conversion of Methanol into 1,1-Dimethoxymethane: Remarkably High Productivity Over an FeMo Catalyst Placed Under Unusual Conditions," Electronic Supplementary Information, Green Chem., 2010, 12, pp. 1-6.

Weissermel, K. et al., Industrial Organic Chemistry, 3rd Completely Revised Edition, 1997, 481 pgs.

Lei, Z. et al., "Synthesis of Dimethyl Ether by Catalytic Distillation," Chemical Engineering Technology, (2011), v. 66, Issue 14, pp. 3195-3203.

Zhang, X. et al., "Synthesis of Methylal by Catalytic Distillation," Chemical Eng. Research and Design 89 (2011), pp. 573-580.

Arpe, H,-J. et al., "Carbonylation to acetic acid," Industrial Organic Chemistry, 4th revised edition 2003, pp. 177.

Arpe, H,-J. et al., "Vinyl acetate@535C," Industrial Organic Chemistry, 4th revised edition 2003, pp. 235.

Arpe, H,-J. et al., "Vinyl ethers to acetals," Industrial Organic Chemistry, 4th revised edition 2003, pp. 238.

* cited by examiner

FACILITATED OXYGENATE SEPARATIONS AND SYNTHETIC FUEL PRODUCTION VIA REACTIVE DISTILLATION

CROSS-REFERENCE TO RELATED APPLICATIONS

This application is the U.S. national phase of PCT Application No. PCT/US2015/020740 filed Mar. 16, 2015, which claims the benefit of U.S. Provisional Application Ser. No. 61/953,826 filed Mar. 15, 2014, the disclosures of which are incorporated in their entirety by reference herein.

TECHNICAL FIELD

In at least one aspect, the present invention relates to methods and equipment for partially oxidizing a hydrocarbon feed gas.

BACKGROUND

The development of oil fields worldwide is accompanied by flaring of a natural gas which results in lost revenue. In addition to this loss, the wasted gas is accompanied by a sizeable amount of pollutants (e.g., methane and carbon dioxide) that are released to the atmosphere. Presently, there is no efficient way of capturing these gases. The World Bank estimates that 140 billion $m^3$ of natural gas are flared annually, an amount equivalent to 20% of the U.S. annual gas consumption.

Currently, there is no fully developed economically effective method for capturing the release gases at isolated wells. Although gas collection seems to be an obvious strategy, gas collection requires an infrastructure of pipelines and compressor stations that are too costly to construct and maintain. Moreover, extracting liquefiable $C_3+$ components only makes a minor improvement to the problem since methane in general cannot be collect. Indeed, methane usually accounts for more than 75% wt. of the uncollected natural gas.

Partially oxidation processes provide a potential method for recapturing alkanes and in particular, methane. Currently, direct homogeneous partial oxidation (DHPO) produces a variety of oxygenates such as alcohols and aldehydes, and carboxylic acids in smaller concentrations. Conversion of these liquid products into higher value fuels and chemicals via process integration is of great interest since process integration permits for cost reduction and therefore applicability at smaller scale. Increasing the carbon length of the alkane feed gas to partial oxidation processes is known to produce higher proportions of alcohols, aldehydes and carboxylic acids having a carbon length greater than one carbon. Many of these components have relative volatilities at standard temperature and pressure similar to that of water thereby complicating separations with conventional techniques. Furthermore, formaldehyde reversibly forms methylene glycol and hemi-formal polymers that can interfere with recovery of high boiling alcohols. The unseparated blend which typically includes water, methanol, formaldehyde, ethanol, acetone, isopropanol, acetaldehyde, formic and acetic acids, and corresponding acetals and esters has little direct value as a fuel in internal combustion engines. Traditional means of separating this blend into individual components and thereby upgrade its fuel and chemical value has been problematic as is known to those skilled in the art.

The prior art separation schemes for blended oxygenates tend to be complicated. For example, azeotropic distillation to separate blends of partially oxidized products. Azeotropic distillation involves complexity relating to the use of additional solvents, higher flow rates, and additional vessels. Therefore, these separations are wasteful from both a capital and operational expense perspective. U.S. Pat. No. 2,710,829 details a method to separate a mixture of alcohols, aldehydes, ketones, and esters. This patent describes a process that uses over ten columns, many of which include azeotropic distillations, to separate the individual oxygenate components. These capital intensive distillation schemes are a primary reason that acetic acid formed by carbonylation of methanol is favored over butane oxidation. (Arpe, H. J. et al, Industrial Organic Chemistry 5th ed. (2010) p. 183). Moreover, even after separation from the partial oxygenate blend, mixed alcohols have limited marketability. For example, methanol is currently of lower value on a weight basis.

Accordingly, there is a need for improved methods for processing blends of partially oxygenated compounds into products that have improved value as a fuel.

SUMMARY

In at least one embodiment, the present invention provides a method for forming a blend including ethers and esters from a blend of partially oxygenated compounds. The method includes a step of reacting a hydrocarbon-containing gas (or blend thereof) with an oxygen-containing gas in a reactor to form a first product blend. The first product blend includes partially oxygenated organic compounds. The blend of partially oxygenated organic compounds is provided to one or more reactive distillation stations. The blend of partially oxygenated compounds is converted to a second product blend at one or more reactive distillation stations. Characteristically, the second product blend includes a mixture comprising at least two components selected from acetals, ethers, alcohols, diols, ketones, esters, alkenes, and combinations thereof.

In another embodiment, an apparatus for forming a blend including ethers and esters is provided. The apparatus includes a reactor and at least one reactive distillation station in fluid communication with the reactor. A hydrocarbon-containing gas reacts with an oxygen-containing gas to form a first product blend in the reactor. The first product blend includes partially oxygenated organic compounds. The reactive distillation station converts the blend of partially oxygenated organic compounds to a second product. The second product blend includes a mixture comprising at least of components selected from acetals, ethers, alcohols, diols, ketones, esters, alkenes, and combinations thereof.

In another embodiment, a method for forming a blend of partially oxygenated compounds is provided. The method includes a step of reacting a hydrocarbon-containing gas (e.g., flare gas) with an oxygen-containing gas to form a first product blend in a reactor. The hydrocarbon-containing gas includes at least two components selected from the group consisting of methane, ethane, proprane, butane, and pentane. The first product blend including acetone, methanol, ethanol, isopropanol, acetic acid, formic acid, formaldehyde, and water.

In still another embodiment, an apparatus for forming a blend of partially oxygenated compounds is provided. The apparatus includes a reactor in which a hydrocarbon-containing gas reacts with an oxygen-containing gas in a reactor to form a first product blend. The apparatus also includes one or more separation stations that receives the first product blend to obtain a second blend of oxygenates. The hydrocarbon-containing gas includes at least two components selected from the group consisting of methane, ethane, proprane, butane, and pentane. The first product blend includes acetone, methanol, ethanol, isopropanol, acetic acid, formic acid, formaldehyde, dimethoxymethane, 1,1 dimethoxyethane, methyl formate, methyl acetate, and water.

In another embodiment, the present invention provides an apparatus that uses reactive distillation to selectively remove formaldehyde as dimethoxymethane in the overhead, formic acid as methyl formate, and acetic as methyl acetate. Moreover, the apparatus produces ethers and potentially unsaturated hydrocarbons in the overhead while concentrating water in the bottoms. Advantageously, the blend of ethers is a value added product that may be used to make other useful compositions by reactions with diols such as a diesel fuel substitute or blending additive or an liquefied petroleum gas (LPG) additive without further reactions.

In still another embodiment, an apparatus for producing one or more oxygenates is provided. The apparatus includes a reactor in which a hydrocarbon-containing gas is reacted with an oxygen-containing gas to form a first product blend. The apparatus also includes at least one reactive distillation station in fluid communication with the reactor. The first product blend includes partially oxygenated organic compounds. At least one reactive distillation station converts the first product blend to a second product. The second product blend includes a mixture comprising at least two of components selected from acetals, ethers, alcohols, ketones, esters, and alkenes.

In yet another embodiment, an apparatus for producing one or more oxygenates is provided. The apparatus includes a reactor in which a hydrocarbon-containing gas is reacted with an oxygen-containing gas to form a first product blend. The apparatus also includes one or more separation stations that receive the first product blend to obtain a second blend of oxygenates. The hydrocarbon-containing gas includes at least two components selected from the group consisting of methane, ethane, proprane, butane, and pentane. The first product blend includes acetone, methanol, ethanol, isopropanol, acetic acid, formic acid, formaldehyde, dimethoxymethane, 1,1 dimethoxyethane, methyl formate, methyl acetate, and water. The second blend of oxygenates includes 0 to 15 mole percent acetone, 30 to 99 mole percent methanol, 0 to 20 mole percent ethanol, 0.0 to 10 mole percent isopropanol, 0 to 1 mole percent acetic acid, 0 to 1 mole percent formic acid, 0 to 15 mole percent formaldehyde, and 1 to 30 mole percent water.

DETAILED DESCRIPTION

Figure 1:
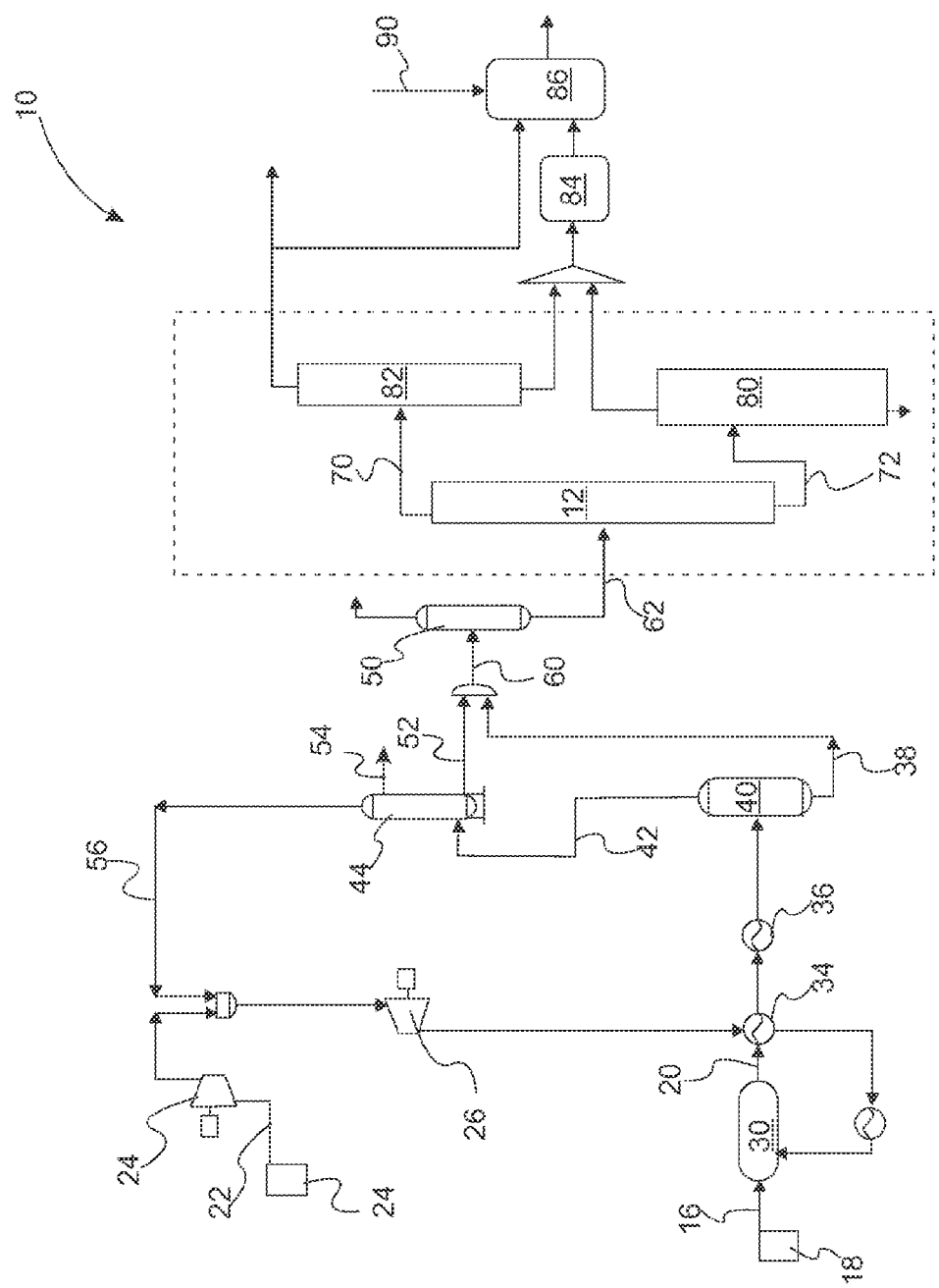
FIG. 1 is a schematic illustration of a system for forming a blend of acetals, esters, ethers, and potentially unsaturated hydrocarbons using a reactive distillation component.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred.

Also, unless expressly stated to the contrary: percent, "parts of," and ratio values are by moles; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The presented invention incorporates a gas to chemicals and synthetic fuels process with alcohol acetalization, esterification, etherification, and dehydration by reactive distillation of a raw oxygenate blend. Characteristically, the process removes components such as alcohols, aldehydes, and carboxylic acids as high relative volatility components (overhead components) by a first reactive distillation station that has a reactive distillation column. Advantageously, these volatile condensation products can be recovered for use as a fuel for compression ignition engines or for their constituent chemical value such as for solvents. The bottoms product (i.e., the liquid products not removed in the overhead) from the reactive distillation column in the first reactive distillation system is directed to a regular distillation column (i.e., simple or fractional distillation) to recover remaining alcohols not recovered in in the first reactive distillation station (e.g., a mixture of $C_1$ to $C_4$ alcohols). The $C_4$ and higher alcohols can be recovered from the bottoms of this column due to phase separation. The isolated mixed alcohols in the distillate of the second regular distillation can be used alone for their fuel value or further converted to ethers and possibly olefins in a third etherification station with a reactive distillation column (i.e., a second reactive distillation station). Recovered alcohols (e.g., the mixture of $C_1$ to $C_4$ alcohols or $C_4$ and higher alcohols) from the regular distillation column and the acetals produced in the first reactive distillation column can then undergo a transacetalization reaction. In a refinement, these recovered alcohols and acetals are reacted together in the transacetalization reaction.

Ethers are well known hydrocarbon fuel substitutes that can be efficiently produced by a reactor/reactive distillation combination. The overhead in the reactive distillation column will contain light alcohols ($C_1$ and possibly $C_2$), acetals such as dimethoxymethane (DMM), esters such as methyl acetate or formate, and ketones such as acetone. The alcohol content of this stream can be separated and potentially reacted to make more acetals or directed to an etherification station to form ethers. The ether, alcohol, and acetal products are of ideal composition to undergo further reactions in order to make a high cetane diesel substitute and/or additive. Finally, a blend of these recovered alcohols and produced ethers and acetals can be added to diols to produce glymes. Ethers, especially dimethyl ether, suffer from having high volatility and low lubricity. Glymes such as 1,2 dimethoxyethane or 1,2 dimethoxypropane are known to have very high cetane numbers and better lubricity. Furthermore, glymes can be blended with the methylal (i.e., DMM) produced in the reactive distillation column to form a substitute diesel blend or diesel additive. In a refinement, diols are produced by a reaction with biomass derived polyols via biomass hydrogenation. The diols used in the process can be produced by using polyol feed such as cellulose, starch, $C_6$ and $C_5$ sugars, or glycerol. Moreover, the glyme precursors can also be produced by dimethoxymethane carbonylation and hydrogenation. This facilitated separation through selective production of light acetals, esters and/or ethers decreases energy and equipment demands. In this context light means 5 carbon atoms or less (e.g., 5, 4, 3, or 2 carbon atoms).

With reference to FIG. 1, a process and related apparatus for converting a blend of alcohols to a blend (i.e., a mixture) of ethers, aldehydes, ketones, and organic acids by reactive distillation. In a refinement, the apparatus 10 functions in a continuous manner when in operation in which the products from one component flow to a downstream component. In a refinement, a blend of $C_{1-10}$ alcohols is converted to a blend of $C_{2-20}$ ethers. In another refinement, a blend of $C_{1-4}$ alcohols is converted to a blend of $C_{2-8}$ ethers. Examples of suitable alcohols include, but are not limited to, methanol, ethanol, propanols (e.g., n-propanol, iso-propanol), butanols (e.g., sec-butanol, tert-butanol, iso-butanol), pentanols, and combinations thereof, and the like. Examples of suitable aldehydes include formaldehyde, acetaldehyde, propionaldehyde, and butyraldehydes. Examples of suitable acids include formic, acetic, and propanoic acid. Examples of suitable ketones include acetone and butanone.

In a variation, apparatus 10 produces the blend of alcohols in a continuous fashion while continuously providing (i.e., flowing) the alcohol blend to reactive distillation station 12. A blend of acetals, esters and ethers is formed in reactive distillation station 12. The blend of alcohols is produced by a gas-to-chemicals process in which a reactant stream including the hydrocarbon-containing gas composition 14 is partially oxidized by an oxygen containing gas 16 from oxygen-containing gas source 18 to form first product stream 20. In a refinement, hydrocarbon-containing gas 14 includes hydrocarbon gas 22 from source 24 which optionally passes through compressors 24 and 26. In a refinement, the reaction is operated at pressures from about 450 to 1250 psia and temperatures from about 350 to 450° C. The hydrocarbon-containing gas composition 14 and the oxygen-containing gas 16 are each flowed to reactor 30. Examples of systems and methods of performing the partial oxidation as set forth in U.S. Pat. Nos. 8,293,186; 8,202,916; 8,193,254; 7,910,787; 7,687,669; 7,642,293; 7,879,296; 7,456,327; and 7,578,981; the entire disclosures of which are hereby incorporated by reference.

In a refinement, the hydrocarbon-containing gas 14 includes $C_{1-10}$ alkanes. In another refinement, the hydrocarbon-containing gas includes an alkane selected from the group consisting of methane, ethane, propanes, butanes, pentanes and combinations thereof. In another refinement, the hydrocarbon-containing gas includes an alkane selected from the group consisting of methane, ethane, and combinations thereof. Examples of oxygen containing gas include molecular oxygen which may be in the form of concentrated oxygen or air.

In a refinement, first product stream 20 (i.e., blend) includes $C_{1-10}$ alcohols, $C_{1-3}$ aldehydes, $C_{3-4}$ ketones, and $C_{1-2}$ carboxylic acids, and their corresponding dehydration products such as $C_{2-12}$ esters and $C_{3-24}$ acetals. In particular, first product stream 20 includes an alcohol selected from the group consisting of methanol, ethanol, propanols, butanols, and combinations thereof. In a further refinement, the first product blend also includes a component selected from the group consisting of methanol, ethanol, formaldehyde, acetaldehyde, acetone, formic acid, acetic acid, methyl and ethyl acetates and formats, dimethoxymethane, 1,1 dimethoxyethane, and combinations thereof. In particular, the acetals may include dimethoxymethane.

Following the partial oxidation reaction, the product stream 20 is provided to and rapidly cooled in a series of heat exchangers 34 and 36 to prevent decomposition of the produced oxygenates and for separation of the liquid fraction (i.e., the alcohols in the blend of alcohols). Reactor 30 is in fluid communication with heat exchangers 34 and 36. After cooling first product stream 20 at the heat exchangers, the formed liquids 38 are separated from the gas stream at separation station 40 which are sent to station 50 (e.g., a flash drum). The gas stream 42 is then provided to purification station 44 where a separation process for removal of non-hydrocarbon fractions (e.g., nitrogen) from hydrocarbon fractions is performed. Purification station 44 may remove the non-hydrocarbon fractions by scrubbing, membrane separation, adsorption processes, cryogenic separations, or by purging a small gas fraction. If station 44 is a liquid scrubbing system, liquid products 52 are sent to a station 50 where dissolved gases are removed. Non-hydrocarbon gases are removed from the recycle loop via output 54, and the hydrocarbon gases 56 are then recycled to combine with fresh hydrocarbon gas 22 which has been pressurized to the pressure of the loop by compressor 24. The stream composed of recycled hydrocarbons plus fresh methane gas is pressurized to make up for pressure losses in the recycle loop via compressor 26, preheated via the cross exchanger 34 and further by the preheater 58, when necessary, to meet the desired reaction conditions. Liquids 52 recovered from station 44 and liquids 38 can be combined to form liquid stream 60 which is directed to station ultimately to reactive distillation station 12.

Liquid stream 60 generated by this gas-to-chemicals process is composed predominantly of alcohols, aldehydes and water, more specifically methanol, ethanol, formaldehyde and water. Basic separation of alcohols occurs via reactive distillation. These streams may then be subjected to further separation processes for acquiring individual products at their desired purities. Because the gas-to-chemicals process operates at high pressures, there is no need for re-pressurization of the liquid stream for dimethyl ether (DME) synthesis. In a refinement, in order to prevent formaldehyde from vaporizing in the distillation column bottom, formaldehyde is removed from liquid stream 60 to form liquid stream 62 prior to reactive distillation. Formaldehyde can be removed using a selective scrubbing solution or a reactive scrubbing solution for either the aldehyde or alcohol fraction in station 50. In a refinement, station 50 operates at pressures of 0 to 200 psia, more preferably 14.7 to 150 psia, and at temperatures of 0 to 300° C. more preferably 40 to 15° C. In another refinement, formaldehyde hydrates may be submitted to the reactive distillation column 12 together with the alcohol fraction.

The present embodiment advantageously uses reactive distillation station 12 for conversion liquid stream 60 and/or liquid stream 62 to a specific blend of lighter oxygenates. Liquid streams 60, 62 include a blend of alcohols. Reactive distillation station 12 is in fluid communication with reactor 30 as well as heat exchangers 34 and 36. In particular, the present embodiment uses reactive distillation for the conversion of a methanol or a methanol/ethanol blend to dimethyl ether or an ether blend resulting from dehydration of both methanol and ethanol fractions. In a refinement, the first product blend is converted to esters such as the methyl ester of $C_{1-2}$ acids.

To eliminate the undesirable products (formaldehyde HCHO and organic acids RCOOH) from liquid stream 60 and/or liquid stream 62, acetalization and esterification reactions are conducted in reactive distillation station 12 in accordance with the following equations:

$$HCHO + 2CH_3OH \leftrightarrow CH_3OCH_2OCH_3 + H_2O \qquad \text{Eq. 1}$$

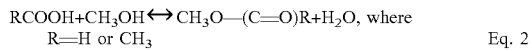

$$RCOOH + CH_3OH \leftrightarrow CH_3O\text{---}(C\text{=}O)R + H_2O, \text{ where } R\text{=}H \text{ or } CH_3 \qquad \text{Eq. 2}$$

Figure 2:
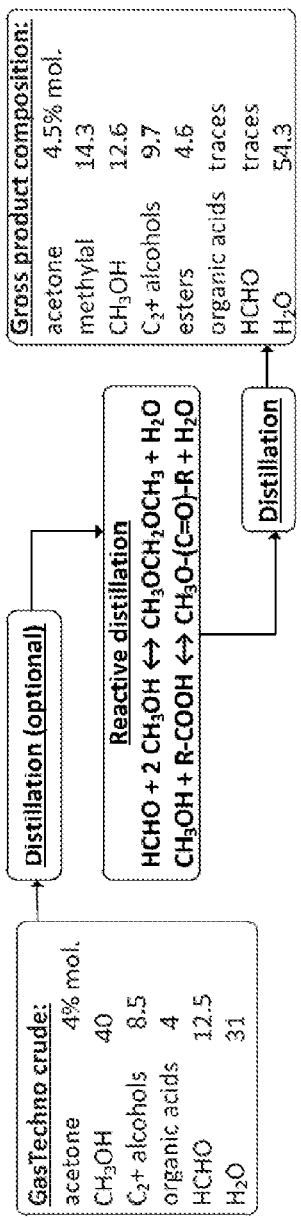
FIG. 2 is a schematic of showing products that can be obtained using reactive distillation followed by simple distillation

It should be appreciated that these reactions are reversible. Moreover, isolation of the products (e.g., water, methylal, and esters) by distillation will drive the reactions to completion. Methanol, as the most reactive alcohol in the blend (ethanol and isopropanol are others), is the primary reagent for both reactions. The reactions of equations 1 can be driven to near completion by using a high molar ratio $CH_3OH:HCHO$ (from about 2:1 to 4:1 or about 2.8) thereby increasing the HCHO conversion in acetalization. Similarly, the reactions of equation 2 can be driven to completion by using a high molar $CH_3OH:RCOOH$ (typically, from about 2:1 to about 12:1 with 10:1 being typical). These reactions can advantageously proceed in mild conditions (~atmospheric pressure, <100° C.) on the same solid acidic catalyst (e.g., $H^+$-form of a strong acid cation exchange resin). Side reactions (e.g., etherification of methanol into dimethyl ether) can be suppressed by relatively low values of the targeted temperature and pressure. FIG. 2 provides an example of products that can be obtained using reactive distillation followed by simple distillation. If advantageous for the efficiency of the overall process, additional distillation step can be used for fractionating liquid stream 60 and/or liquid stream 62 before the reactive distillation. In a refinement, chemical conversion of liquid stream 60 and/or liquid stream 62 is performed in a reactive distillation column having a layer of catalyst centrally placed in the column. Following the distillation step, the converted crude is converted into commercially valuable products, including diesel fuel additive (e.g., methylal), general-use solvents and chemicals (e.g., methylal, acetone, esters); pipeline corrosion inhibitor (e.g., methanol and $C_2+$ alcohols); motor alcohol fuels and gasoline additives (e.g., methanol and $C_2+$ alcohols); and water with traces of HCHO and acids, and with the small amounts of alcohols and esters (suitable for preparing the drilling muds).

The reaction of methanol to form dimethoxymethane (DMM, methylal) is usually an acid catalyzed reaction with methanol and formaldehyde. In particular, solid-state sulfonic acid functionalized polymers such as Nafion® and Amberlyst®, Lewis acids such as zirconium sulfate, acidic zeolites, and acid functionalized ionic liquids can be used catalyze to catalyze ether, esters, and/or acetal formation in the reactive distillation column(s). Solid acid catalysts can be embedded within structured packing (see, Synthesis of Methylal by Catalytic Distillation, Zhang, Zuemei et al, Chemical Engineering Research and Design) that is positioned internally in the reactive distillation column(s). By using ether or acetal or ester forming transformations in one or more reactive distillation columns, aldehyde azeotropes can be avoided and the volatility of the mixture to be distilled increase. Moreover, these reactions are typically conducted at lower temperatures and pressures than traditional methods for separating these compounds. In the context of a first reactive distillation column, aqueous formaldehyde in the raw blend feed reacts under acidic conditions with methanol to produce the high relative volatility dimethoxymethane. Although formaldehyde will react with higher alcohols such as ethanol under these conditions, dimethoxymethane will preferentially concentrate on higher trays as again it is the most volatile acetal. Depending on the feed and degree of oxidation, substantial amounts of acetic acid can be produced which will be recovered from the partial oxidation process in the raw blend. Acids such as formic acid concentrate in the bottoms of a non-reactive atmospheric distillation column designed to separate methanol and ethanol from water. Reactive distillation can be used to convert the acids and alcohols via acid catalyzed condensation reactions to more volatile esters. The formed volatile esters will concentrate towards the top of the column.

With reference to FIG. 1, a variation of distillation column 12 includes a catalyst-packed column where reactive distillation is performed. In a refinement, the reactive distillation is operating at pressures between 0 and 250 psia, preferably between 14.7 and 150 psi. The catalyst used in the packed column catalyzes the conversion of alcohols to ethers. In a refinement, the catalyst is an immobilized catalyst. Examples of such catalysts include, but are not limited to, aluminosilicate catalysts, copper modified alumina catalyst, combinations thereof and the like. At these elevated pressures the boiling point of methanol is increased to the preferred temperatures for alcohol dehydration, between 50 and 300° C. and preferably between 150 and 250° C. Temperatures may be controlled so as to dehydrate only the methanol fraction to DMM, or the methanol and ethanol fraction to an ether blend.

Ethers are obtained from the column distillate 70 and water from the column bottoms 72 when formaldehyde has been removed from the process stream 62 prior to reactive distillation. In a refinement, reactive distillation station 12 includes one or more adiabatic reactors or radial flow adiabatic fixed bed reactors. Examples of suitable reactive distillation stations and adiabatic beds are commercially available from E. I. du Pont de Nemours and Company, Haldor Topsoe, and Toyo Engineering Corporation.

In certain variations, an aqueous formaldehyde solution (i.e., less than 37% formaldehyde in water) or formalin is present in process stream 62, formaldehyde will exit the reactive distillation column together with the ethers (e.g., DME or the ether blend) in the distillate 70. Therefore, in a refinement, downstream separation of formaldehyde from DME or the ether blend can be performed to obtain pure products and products of higher value.

The raw blend entering reactive distillation station 12 will may contain the following molar composition (i.e., mole percentages): water: 0-70 mole %; methanol: 20-70 mole %; formaldehyde: 0-40 mole %; ethanol: 0-50 mole %; isopropanol: 0-20 mole %; acetone: 0-20 mole %; acetic acid: 0-20 mole %; formic acid: 0-20 mole %. In a refinement, the raw blend includes water: 5-50 mole %; methanol: 20-50 mole %; formaldehyde: 1-20 mole %; ethanol: 1-20 mole %; isopropanol: 1-10 mole %; acetone: 1-10 mole %; acetic acid: 1-10 mole %; formic acid: 1-10 mole %. It should be appreciated that esters and acetals of this composition can form in-situ from the respective stoichiometry of this composition due to the acidic nature of the liquid.

The raw blend recovered from the separator and potentially scrubbers is directed to reactive distillation column 12. Optionally, these liquids can travel through a tubular reactor to achieve partial conversion prior to reactive distillation column 12.

Acetone will also concentrate in the distillate of the column 12 along with methyl acetate, methyl formate, DMM, and some methanol. This forms a first volatile distillate stream that is directed to separator 82. Higher alcohols and water are recovered off the bottom of column 12 and are directed to column 80.

The column 12 bottoms product 72 will contain dilute mixed alcohols and water. A substantial fraction of the acetic acid and formaldehyde will have been converted in column 12 and recovered in the overhead. The column 12 bottoms stream is directed to column 80. In column 80, mixed alcohols such as the remaining methanol, isopropanol, ethanol, and some butanol are recovered in the overhead distillate. The bottoms product will consist primarily of water and potentially some $C_{4-8}$ oxygenates. In a refinement, a portion of these oxygenates are recoverable due to liquid phase separation. In this aspect, the present apparatus is used to treat the water rejected in the column 82 bottoms. In a refinement, column 80 may not be necessary depending on the composition of the raw blends and recovery performance of column 12.

As hydrated and/or polymerized formaldehyde is known to concentrate in tertiary solutions of water and alcohol as a bottoms product, this formaldehyde would be treated in waste water treatment were it not for column 12. In small scale applications, waste water treatment can form a significant expense. Furthermore, low levels of formaldehyde inhibit microbe growth such as those that might be desired to metabolize dilute oxygenate components. As the formaldehyde and a portion of would be recovered as acetals, hydrated formaldehyde products would not concentrate to the same extent in the bottoms. Furthermore, the water generated by the condensation reactions can be utilized onsite for utility purposes. In arid regions, this can be a significant benefit.

The overhead of column 80 will contain mostly methanol, with some ethanol, isopropanol, and possibly butanol. If ethers are desired, this mixed alcohol stream is direct to pre-etherification reactor 84 where these alcohols are converted into ethers at an equilibrium concentration in the presence of catalysts. Examples of such catalysts include, but are not limited to, $\gamma$-$Al_2O_3$, modified alumina catalysts, H-ZSM-5, zeolites, and ion exchange resins, and combinations thereof and the like. Examples of suitable catalysts are set forth in *Synthesis of dimethyl ether by catalytic distillation*, Lei, Zhigang et al, Chemical Engineering Technology, vol. 66, Issue 14, p. 3195-3203 (2011), the entire disclosure of which is hereby incorporated by reference. At elevated pressures in reactor 84, the boiling point of methanol is increased to the preferred temperatures for alcohol dehydration, between 50 and 500° C. and preferably between 250 and 450° C. Pressure can range between 0 and 500 psig. Temperatures may be controlled so as to dehydrate only the methanol fraction to DME, or the methanol and ethanol fraction to an ether blend. Reactor 84 effluent will contain an equilibrium mixture of ethers, alcohols, and water. It may also contain some unsaturated hydrocarbons due to full dehydration of the alcohol. This mixture is directed to reactor 86, where reactive distillation in the presence of a second catalyst again takes place this time completing the etherification of the reactor 84 effluent. Suitable second catalysts include sulfonic acid resins such as sulfonic acid functionalized cross-linked polystyrene, such as the Amberyst® series of polystyrene, fluorosulfonic polymer such as Nafion® and free organic sulfonic acids such as toluene, methane, or halomethane sulfonic acids. Pressure in reactor 86 can be from 0 to 300 psig, more preferably below 150 psig in order to limit catalyst deactivation by decomposition as might occur with ion exchange catalysts with sulfonic acid functionality at temperatures over 140° C.

The volatile overhead from column 12 can undergo further separations such as distillation or pervaporation to separate the methanol and concentrate the esters and acetals. In a refinement, methanol is converted into ethers and/or acetals in a single step reaction. Column 82 is used for this purpose. In a refinement, column 82 is regular distillation column (i.e., simple or fractional distillation). The concentrated methanol stream may optionally be oxidized to DMM. This can be performed using standard FeMo (iron-molybdenum) methanol oxidation to formaldehyde catalysts (Direct control of methanol into 1,1 dimethoxy methane: remarkably high productivity of an FeMo catalyst placed under unusual conditions, Gornay, Julien et al, Green Chemistry). At 260° C. and a methanol rich feed, DMM was produced at a 56% conversion and 90% selectivity to DMM. Further patents such as U.S. Pat. Nos. 4,501,917 and 7,772,423 describe acid catalyzed processes to form methyl methoxyacetate, which can be hydrogenated to yield 2-methoxymethanol, a precursor to monoglyme or methyl vinyl ether. The entire disclosures of these patents are hereby incorporated by reference. In other variations, the recovered methanol can be reacted directly to form acetals preferably in a single step.

Alternatively, the column 12 overhead can be mixed with alcohols or ethers produced in column 82 or column 80. This mixture can be directed to reactor 86. In reactor 86, etherification and trans-etherification reactions take place in an acid catalyzed plug flow reactor (PFR) or continuous stirred tank reactor (CSTR). Conditions necessary to perform this are described in U.S. Pat. No. 4,579,980. Biomass derived or oxygenate derived diols can also introduced here. Products formed from in apparatus 10 include 1,2 dimethoxyethane, 1,2 dimethoxy propane, 1,3 dioxolane, 1,4 dioxane, 4-methyl-1,3-dioxolane, 1-methoxy-2-propanol, 2-methoxy-1-propanol, 2-methoxyethanol, dialkyl ethers and dialkyl acetals. Ethoxy, propoxy, and butoxy analogs of these compounds are also possible. Alcohols with alkoxy functionality, such as alkoxy ethanol or alkoxy propylene glycol are especially desirable, as are dialkoxy propylene glycols. In a refinement, polyols 90 are provided to reactor 86.

In a refinement, reactor 86 includes catalysts for etherification, transetherification, and transacetalization. Examples of suitable catalysts are described in U.S. Pat. No. 4,579,980 which describes heteropoly acids such as and supported heteropoly acids. Heteropoly acids are macromolecular assemblages with usually a central hetero atom such but not limited to as silicon, phosphorous, boron, germanium, titanium, manganese, arsenic, etc. The hetero atom coordinates with a poly atom, often molybdenum or tungsten, and oxygen to form various crystalline structures such.

Preferably, this catalyst is immobilized on a solid support. Typical reaction conditions are 100-200 C and 100-500 psig. Other solid acid catalysts may be employed as well, especially when the desired reactions include only transacetalizaiton and transesterification. In this case, catalysts such as those mentioned as suitable for reactive distillation column 12 may be suitable. In this manner, acetals such as those recovered in the column 12 overhead or subsequently formed may be reacted with higher alcohols under the same acid catalyzed conditions sufficient for acetalization. In such a transacetalization reaction, dimethoxymethane produced and recovered in the column 12 overhead, and optionally dimethoxy methane produced with the methanol recovered in the column 12 overhead will react with higher alcohols to produce acetals with improved properties for compression ignition engines over DMM. If the higher alcohols include ethanol, isopropanol, and butanol, the acetals formed will also include these alcohols in their respective alkoxy groups. Similarly, esters such as methyl acetate may transesterify with ethers and/or ethers having an alcohol functionality and in particular, mono ethers such as 1-methoxy-2-propanol or 2-methoxymethanol to produce an oxygenated ester such as 1-methoxy-2-propanol acetate or 2-methoxymethyl acetate. These compounds are suitable for use in compression ignition engines or an oxygenated additive. Alternatively, these compounds can be cracked to form alkyl vinyl ethers and carboxylic acids. In a refinement, ethers with OH functionality are dehydrated to form alkyl vinyl ethers. In a further refinement, alkyl vinyl ethers are oligomerized to form short chain polyvinyl ethers that may be used as a fuel in compression ignition engines. Moreover, the formed esters can be used in compression ignition engines, for example as a fuel.

The esters, ethers, and acetals formed in the method and apparatus set forth above can be use to form a number of value added produces and/or provide efficient formation for these compounds. For example, the transesterification of methyl acetate with alkoxyalcohols can bypass one method of their formation as described by U.S. Pat. No. 6,090,988, where alkoxyalcohols are thermally dehydrated over a supported alkali catalyst. The entire disclosure of this patent is hereby incorporated by reference. Azeotropic distillations are necessary to recover the unreacted alkoxyalcohol, as alkoxyalcohols form azeotropes with water. It should be noted that water is necessarily produced in the reaction. U.S. Pat. No. 5,773,669 describes a reaction in which alkoxyalkyl esters can be thermally split into vinyl ethers and free acid; the entire disclosure of this patent is hereby incorporated by reference. U.S. Pat. No. 5,773,669 describes the formation of ester from acetic anhydride as wasteful. However, transesterification using solid acid catalysts is a common practice for biodiesel transesterification to recover fatty acid methyl esters from triglycerides thereby producing glycerol. Similar reactions can similarly recover acetic acid esters of alkoxyalkanols from methyl acetate thereby producing methanol. Methanol formed in this manner can potentially be recovered via pervaporation membrane. The remaining methyl acetate and methanol could be distilled as an azeotrope and fed back to column 12. Similarly, the recovered acetic acid following alkoxyalkyl ester cracking can be fed back through column 12.

Conditions for cracking alkyl esters such as those formed above to yield unsaturated products are described in patents and literature. Ethylene glycol diacetate can be cracked to vinyl acetate at 535° C. (H J Arpe et al. Industrial Organic Chemistry, 5 ed, pp 239). U.S. Pat. No. 4,399,305 describes the pyrolysis of ethyl acetate to yield ethylene. The entire disclosure of this patent is hereby incorporated by reference. This is performed over perfluorsulfonic acid catalysts such as Nafion® at 150 to 250° C. and atmospheric or slightly pressurized environments. According to U.S. Pat. No. 5,579,980, Nafion® is likely to decompose at these temperatures, so it is likely that similar other sulfonic acid functionalized sulfonic acid catalysts would need to be found such as those disclosed in U.S. Pat. No. 4,620,050 where zeolites such as mordenites in acidic, basic, or de-aluminated form decompose ethyl esters of carboxylic acids to recover the free acid and ethylene; the entire disclosure of these patents are hereby incorporated by reference. In an analogous reaction, alkoxyalkyl esters would be dehydrated at 0 to 500 psig and 100 to 700 C, more preferably, 0-100 psig and 150-550 C, to form the respective alkyl vinyl ether and acetic acid. Separation of the products is trivial due to the very high relative volatility of alkyl vinyl ether over acetic acid.

The value of alkyl vinyl ethers is in their utility as intermediates to diesel fuel additives and substitutes. For example, acetals can be created from alkyl vinyl ethers. (H J Arpe et al. Industrial Organic Chemistry, 5 ed, p. 242). Alternatively, alkyl vinyl ethers, can oligomerize to create short chain polyethers. These oligomers have increased utility over ethylene oxide oligomers in their lack of alcohol (OH) functionality. Furthermore olefins, such as those obtained by methanol to olefins, could oligomerize with alkyl vinyl ethers. In a variation, a diesel fuel using these components includes oligomerized alkyl vinyl ether present in an amount from about 10 to 100 mole percent, propyleneglycol dimethyl ether present in an amount from about 0 to 50 mole percent, and dialkyl acetal present in an amount from about 0 to 25 mole percent.

In another embodiment, a method for forming a blend of partially oxygenated compounds is provided. The method includes a step of reacting a hydrocarbon-containing gas with an oxygen-containing gas to form first product blend 20 in reactor 30 of FIG. 1. The hydrocarbon-containing gas includes two components selected from the group consisting of methane, ethane, proprane, butane, and pentane. In a refinement, the hydrocarbon-containing gas includes methane and ethane. In a refinement, the hydrocarbon-containing gas includes three components selected from the group consisting of methane, ethane, proprane, butanes, and pentanes. In a refinement, the hydrocarbon-containing gas includes methane, ethane and proprane, butane. In another refinement, the hydrocarbon-containing gas includes at least four components selected from the group consisting of methane, ethane, proprane, butane, and pentane. In another refinement, the hydrocarbon-containing gas includes methane, ethane, proprane, and butane. In still another refinement, the hydrocarbon-containing gas includes methane, ethane, proprane, butane, and pentane. In a refinement, the hydrocarbon gas includes 10 to 100 mole percent methane, 0 to 30 mole percent ethane, 0 to 10 mole percent propane, 0 to 5 mole percent butanes (n-butane, isobutane), 0 to 2 mole percent pentanes (n-pentane, neopentane, isopentane). In a still another refinement, the hydrocarbon gas includes 30 to 80 mole percent methane, 2 to 10 mole percent ethane, 0.5 to 5 mole percent propane, 0.1 to 2 mole percent butanes (n-butane, isobutane), 0.02 to 1 mole percent pentanes (n-pentane, neopentane, isopentane). In a yet another refinement, the hydrocarbon gas includes 50 to 65 mole percent methane, 3 to 6 mole percent ethane, 0.5 to 2 mole percent propane, 0.1 to 1 mole percent butanes (n-butane, isobutane), 0.05 to 1 mole percent pentanes (n-pentane, neopentane, isopentane). The first product blend including acetone, methanol, ethanol, isopropanol, formic acid, formaldehyde, and water. In a refinement, the first product further includes dimethoxymethane, 1,1 dimethoxyethane, methyl formate, methyl acetate. In another refinement, the first product blend also includes acetic acid or esters thereof. Typically, the first product blend includes 0 to 10 mole percent acetone, 10 to 60 mole percent methanol, 0.5 to 20 mole percent ethanol, 0.0 to 10 mole percent isopropanol, 1 to 10 mole percent acetic acid, 0.5 to 5 mole percent formic acid, 1 to 20 mole percent formaldehyde, 0 to 3 mole percent dimethoxymethane, 0 to 3 mole percent 1,1 dimethoxyethane, 0 to 3 mole percent methyl formate, 0 to 3 mole percent methyl acetate, and 20 to 60 mole percent water. In a refinement, the first product blend includes 1 to 10 mole percent acetone, 10 to 60 mole percent methanol, 1 to 20 mole percent ethanol, 0.1 to 10 mole percent isopropanol, 1 to 10 mole percent acetic acid, 0.5 to 5 mole percent formic acid, 1 to 20 mole percent formaldehyde, 0 to 3 mole percent dimethoxymethane, 0 to 3 mole percent 1,1 dimethoxyethane, 0 to 3 mole percent methyl formate, 0 to 3 mole percent methyl acetate, and 20 to 60 mole percent water. In another refinement, the first product blend includes 2 to 10 mole percent acetone, 25 to 60 mole percent methanol, 1 to 20 mole percent ethanol, 0.1 to 10 mole percent isopropanol, 1 to 10 mole percent acetic acid, 0.5 to 5 mole percent formic acid, 1 to 20 mole percent formaldehyde, 0 to 3 mole percent dimethoxymethane, 0.02 to 2 mole percent 1,1 dimethoxyethane, 0.02 to 2 mole percent methyl formate, 0.02 to 2 mole percent methyl acetate, and 20 to 60 mole percent water. In still another refinement, the first product blend includes 3 to 10 mole percent acetone and/or 25 to 60 mole percent methanol and/or 1 to 20 mole percent ethanol and/or 0.1 to 10 mole percent isopropanol and/or 1 to 10 mole percent acetic acid and/or 0.5 to 5 mole percent formic acid and/or 1 to 20 mole percent formaldehyde and/or 0.02 to 1 mole percent dimethoxymethane and/or 0.02 to 1 mole percent 1,1 dimethoxyethane and/or 0.02 to 1 mole percent methyl formate and/or 0.02 to 1 mole percent methyl acetate and/or 20 to 60 mole percent water. In a variation, one or more separations stations (e.g., distillation station) such as purification station 44 to obtain a second blend of oxygenates. The second blend of oxygenates including 0 to 15 mole percent acetone, 30 to 99 mole percent methanol, 0 to 20 mole percent ethanol, 0.0 to 10 mole percent isopropanol, 0 to 1 mole percent acetic acid, 0 to 1 mole percent formic acid, 0 to 15 mole percent formaldehyde, and 1 to 30 mole percent water While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:
1. A method for forming a blend including ethers and esters from a blend of partially oxygenated organic compounds, the method comprising:
   a) reacting a hydrocarbon-containing gas with an oxygen-containing gas in to form a first product blend, the first product blend including partially oxygenated organic compounds; and
   b) converting the blend of partially oxygenated organic compounds to a second product blend by a first acid-catalyzed reactive distillation, the second product blend including a mixture comprising acetal and a component selected from ethers, alcohols, ketones, esters, and alkenes.

2. The method of claim 1 wherein the hydrocarbon-containing gas includes $C_{1-10}$ alkanes.

3. The method of claim 1 wherein the hydrocarbon-containing gas includes an alkane selected from the group consisting of methane, ethane, propanes, butanes, pentanes and combinations thereof.

4. The method of claim 1 wherein the hydrocarbon-containing gas includes an alkane selected from the group consisting of methane, ethane, and combinations thereof.

5. The method of claim 1 wherein the first product blend includes $C_{1-10}$ alcohols, $C_{1-3}$ aldehydes, $C_{3-4}$ ketones, and $C_{1-2}$ carboxylic acids, and their corresponding dehydration products such as $C_{2-12}$ esters and $C_{3-24}$ acetals.

6. The method of claim 5 wherein the first product blend includes an alcohol selected from the group consisting of methanol, ethanol, propanols, butanols, and combinations thereof.

7. The method of claim 1 wherein the first product blend includes a component selected from the group consisting of methanol, ethanol, formaldehyde, acetaldehyde, acetone, formic acid, acetic acid, methyl and ethyl acetates and formats, dimethoxymethane, 1,1 dimethoxyethane, and combinations thereof.

8. The method of claim 1 where the second product blend includes dimethoxymethane.

9. The method of claim 1 where the second product blend includes an ester that is a methyl ester of $C_{1-2}$ acids produced by the first acid-catalyzed reactive distillation.

10. The method of claim 9 where a bottoms product of the first acid-catalyzed reactive distillation is subjected to a second regular distillation which recovers alcohols not recovered in the first acid-catalyzed reactive distillation.

11. The method of claim 10 where all or a portion of recovered alcohols in the second regular distillation are converted into ethers.

12. The method of claim 1 wherein an overhead product of the first acid-catalyzed reactive distillation is further separated to recover methanol.

13. The method of claim 12 where the methanol that is recovered is converted into acetals in a single step reaction.

14. The method of claim 12 where the methanol that is recovered is converted into ethers.

15. The method of claim 10 where recovered alcohols from the first acid-catalyzed reactive distillation and acetals produced in the first acid-catalyzed reactive distillation undergo a transacetalization reaction.

16. The method of claim 10 where esters undergo transesterification reactions with ethers having an alcohol functionality to form esters for use in compression ignition engines.

17. The method of claim 1 where the second product blend comprises a component selected from the group consisting of ethers, alcohols, acetals, diols, and combinations thereof.

18. The method of claim 17 where the diols are produced by a reaction with biomass derived polyols via biomass hydrogenation.

19. The method of claim 17 where the diols or are produced by carbonylation of acetals followed by hydrogenation.

20. The method of claim 17 where the ethers with OH functionality are dehydrated to form alkyl vinyl ethers.

21. The method of claim 20 where the alkyl vinyl ethers are oligomerized to form short chain polyvinyl ethers for fuel use in compression ignition engines.

22. A fuel blend comprising:
   oligomerized alkyl vinyl ether present in an amount from about 10 to 100 mole percent;
   propylene glycol dimethyl ether present in an amount of at most 50 mole percent; and
   dialkyl acetal present in an amount of at most 25 mole percent.

23. A method for forming a blend of partially oxygenated compounds, the method comprising:
   a) reacting a hydrocarbon-containing gas with an oxygen-containing gas to form a first product blend, the hydrocarbon-containing gas includes at least two components selected from the group consisting of methane, ethane, proprane, butane, and pentane, the first product blend including acetone, methanol, ethanol, isopropanol, acetic acid, formic acid, formaldehyde, dimethoxymethane, 1,1 dimethoxyethane, methyl formate, methyl acetate, and water.

24. The method of claim 23 wherein the first product blend includes 2 to 10 mole percent acetone, 25 to 60 mole percent methanol, 1 to 20 mole percent ethanol, 0.1 to 10 mole percent isopropanol, 1 to 10 mole percent acetic acid, 0.5 to 5 mole percent formic acid, 1 to 20 mole percent formaldehyde, 0.02 to 2 mole percent 1,1 dimethoxyethane, 0.02 to 2 mole percent methyl formate, 0.02 to 2 mole percent methyl acetate, and 20 to 60 mole percent water.

25. The method of claim 24 further comprising distilling the first product blend to obtain a second blend of oxygenates, the second blend of oxygenates including 0 to 15 mole percent acetone, 30 to 99 mole percent methanol, 0 to 20 mole percent ethanol, 0.0 to 10 mole percent isopropanol, 0 to 1 mole percent acetic acid, 0 to 1 mole percent formic acid, 0 to 15 mole percent formaldehyde, and 1 to 30 mole percent water.

26. The method of claim 23 wherein the hydrocarbon-containing gas includes flare gas.

27. An apparatus comprising:
   a reactor for reacting a hydrocarbon-containing gas with an oxygen-containing gas to form a first product blend, the first product blend including partially oxygenated organic compounds; and
   at least one reactive distillation station in fluid communication with the reactor, the at least one reactive distillation station converting the first product blend to a second product blend, the second product blend including a mixture comprising acetal and a component selected from the group consisting of ethers, alcohols, ketones, esters, and alkenes.

28. An apparatus comprising:
   a reactor for reacting a hydrocarbon-containing gas with an oxygen-containing gas in a reactor to form a first product blend, the hydrocarbon-containing gas includes at least two components selected from the group consisting of methane, ethane, proprane, butane, and pentane, the first product blend including acetone, methanol, ethanol, isopropanol, acetic acid, formic acid, formaldehyde, dimethoxymethane, 1,1 dimethoxyethane, methyl formate, methyl acetate, and water; and
   a reactive distillation station that receives the first product blend to obtain a second blend of oxygenates, the second blend of oxygenates including 0 to 15 mole percent acetone, 30 to 99 mole percent methanol, 0 to 20 mole percent ethanol, 0.0 to 10 mole percent isopropanol, 0 to 1 mole percent acetic acid, 0 to 1 mole percent formic acid, 0 to 15 mole percent formaldehyde, and 1 to 30 mole percent water, the reactive distillation stations including a reactive distillation column having a layer of catalyst centrally placed in the reactive distillation column.

* * * * *